(12) United States Patent
Hell

(10) Patent No.: US 7,430,045 B2
(45) Date of Patent: Sep. 30, 2008

(54) HIGH SPATIAL RESOLUTION IMAGING

(75) Inventor: Stefan Hell, Göttingen (DE)

(73) Assignee: Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 227 days.

(21) Appl. No.: 11/249,098

(22) Filed: Oct. 12, 2005

(65) Prior Publication Data
US 2006/0038993 A1 Feb. 23, 2006

Related U.S. Application Data

(63) Continuation-in-part of application No. PCT/EP04/03767, filed on Apr. 8, 2004.

(30) Foreign Application Priority Data

Apr. 13, 2003 (DE) ............... 103 17 613
Jun. 5, 2003 (DE) ............... 103 25 460

(51) Int. Cl.
G01J 3/30 (2006.01)
(52) U.S. Cl. ............................ 356/317
(58) Field of Classification Search ......... 356/317, 356/369
See application file for complete search history.

(56) References Cited

U.S. PATENT DOCUMENTS

| | | | |
|---|---|---|---|
| 5,162,867 A * | 11/1992 | Kohno ............ | 356/237.5 |
| 5,731,588 A | 3/1998 | Hell et al. ........ | 250/458.1 |
| 6,046,925 A * | 4/2000 | Tsien et al. ....... | 365/111 |
| 2001/0042837 A1 | 11/2001 | Hoffmann ........ | 250/458.1 |
| 2001/0045529 A1 * | 11/2001 | Iketaki et al. ..... | 250/493.1 |

FOREIGN PATENT DOCUMENTS

| | | |
|---|---|---|
| DE | 100 12 462 A1 | 9/2001 |
| WO | WO 95/21393 | 8/1995 |

OTHER PUBLICATIONS

Klar et al. "Subdiffraction resolution in far-field fluorescence microscopy", Jul. 15, 1999, Optical Society of America, Optics Letters, vol. 24, No. 14, pp. 954-956.*

(Continued)

*Primary Examiner*—Kara E Geisel
(74) *Attorney, Agent, or Firm*—Thomas, Kayden, Horstemeyer & Risley, LLP

(57) ABSTRACT

In high spatial resolution imaging, a structure of a sample is marked with a substance selected from a group of substances capable of being repeatedly transferred out of a first state having first optical properties into a second state having second optical properties by means of an optical switch over signal, and capable of returning out of the second state into the first state, the two states differing in at least one criteria. Within areas the sample is transferred into the second state by means of the optical switch over signal with which at least one spatially limited area is purposefully omitted. An optical measurement signal is detected, which is associated with the substance in the first state and which comes out of a detection area including both the area omitted with the switch over signal and areas in which the substance has been transferred into to second state.

25 Claims, 1 Drawing Sheet

OTHER PUBLICATIONS

Lukyanov, et al., "Natural Animal Coloration Can be Determined by a Nonflourescent Green Fluorescent Protein Homolog", The Journal of Biological Chemistry, vol. 275, No. 84, pp. 25879-25882 (2000).

Dickson, et al., "On/Off Blinking and Switching Behaviour of Single Molecules of Green Fluorescent Protein", Nature, vol. 388, pp. 355-358 (1997).

"A digital Fluorescent Molecular Photoswitch", Nature, vol. 420, pp. 757-760 (2002).

Stefan W. Hell, "Increasing the Resolution of Far-Field Fluorescence Light Microscopy by Point-Spead-Function Engineering", Topics in Fluorescence Microscopy; vol. 5, and Plenum Press New York, pp. 361-426 (1997).

Dyba, et al., "Focal Spots of Size $\lambda/23$ Open Up Far-Field Florescence Microscopy at 33 nm Axial Resolution", Physical Review Letters, vol. 88, pp. 163901-1 to 163904-4 (2002).

* cited by examiner

HIGH SPATIAL RESOLUTION IMAGING

CROSS REFERENCE TO RELATED APPLICATIONS

This application is a continuation in part of International Application PCT/EP2004/003767 with an International Filing Date of Apr. 8, 2004 and claiming priority to co-pending German Patent Application No. 103 17 613.6 entitled "Räumlich hochauflösendes Abbilden und Modifizieren von Strukturen", filed on Apr. 13, 2003, to co-pending U.S. patent application Ser. No. 10/420,896 entitled "High spatial Resolution Imaging and Modification of Structures", filed on Apr. 22, 2003, and to co-pending German Patent Application No. 103 25 460.9 entitled "Räumlich hochauflösendes Abbilden", filed on Jun. 5, 2003.

FIELD OF THE INVENTION

This invention relates to a method of high spatial resolution measuring a sample containing a substance. Particularly, the invention relates to a method of high spatial resolution imaging a structure of a sample, the structure being marked with a substance. Particularly the invention relates to such methods comprising the steps of selecting the substance from a group of substances which are capable of being repeatedly transferred out of a first state having first optical properties into a second state having second optical properties by means of an optical switch over signal, and which are capable of returning out of the second state into the first state; of transferring the substance within areas of the sample into the second state by means of the optical switch over signal with which at least one spatially limited area of the sample is purposefully omitted; and of detecting an optical measurement signal, which is associated with the substance in the first state and which comes out of a detection area including both the area purposefully omitted with the switch over signal and areas in which the substance has been transferred into to second state.

DESCRIPTION OF RELATED ART

The spatial resolution of imaging optical methods is in principle set by the diffraction limit (Abbe's limit) at the respective wave length of the relevant optical signal.

In the field of fluorescence microscopy, however, methods are already known by which the spatial resolution in imaging a structure of a sample is effectively made enhanced beyond the diffraction limit by making use of a non-linear relationship between the sharpness of the definition of the effective focal spot and the input intensity of an optical excitation signal. Examples for these methods include multi-photon absorption in a sample and generation of higher harmonics of the input light. Saturation of an optically induced transfer may also be used as a non-linear relationship, like, for example, in case of stimulated emission depletion (STED) of the fluorescent state, and of ground state depletion (GSD).

In both of these methods, which can in principle achieve a molecular resolution, a fluorescence dye, by which the structure of interest of a sample is marked, is transferred into an energy state, from which no fluorescence is (still) possible, everywhere where an optical switch over signal exceeds a characteristic threshold value, which will be referred to as the saturation threshold value in this description. If the spatially limited area, from which a measurement signal is still registered, is defined by an intensity minimum of the optical switch over signal, which has a zero intensity point and which is, for example, produced by interference, its dimensions, and thus the achieved spatial resolution, are smaller than the diffraction limit. The reason is that the spatially limited partial area out of which the measurement signal is registered is delimited with an increasing level of saturation of the depletion of the energy state involved in fluorescence. In the same way, the edge of a focal spot or of an illuminated stripe becomes steeper, which also results into an increased spatial resolution.

A particular STED method is known from WO 95/21393 A1. In this method, a sample or a fluorescence dye by which a structure of interest within the sample is marked is excited for fluorescence by means of an exciting beam. The spatially limited area of the excitation, to which the diffraction limit normally applies, is then reduced in that it is superimposed with an intensity minimum of an interference pattern of a stimulation beam which is used as a switch over signal according to the terminology of this description. Everywhere, where the switch over signal exceeds a saturation threshold value, the fluorescence dye is fully stimulated for stimulated emission, i.e. it is brought down from the previously excited energy state. The remaining spatially limited area out of which fluorescence light is still spontaneously emitted afterwards only correspond to a reduced area around the center of the intensity minimum in which the switch over signal was not present or not present with a sufficient intensity. Although this method of fluorescence microscopy obviously provides a spatial resolution below the diffraction limit, it also has disadvantages. The life time of the energy state of the fluorescence dye excited by the exciting beam is very short only. Thus, a comparatively high intensity of the switch over signal has to be applied for effectively providing the full switching over within the short period of time. The intensity of the stimulation beam has additionally to be very high so that the stimulation by the switch over signal shows a non-linear relationship between the remaining fluorescence and the intensity of the switch over signal, i.e., so that saturation is achieved. Thus, as a rule, a pulsed high power laser is necessary for the stimulation light beam, which makes the application of the known method quite cost-intensive.

These disadvantages also apply to known GSD methods as time limitations and power requirements are here also set by short life times of the involved energy states.

From The Journal of Biological Chemistry, Vol. 275, No. 84, pages 25879-25882 (2000) a protein is known which can increasingly be excited for fluorescence in a red range by means of green light, but which looses its fluorescence properties upon exposition to blue light. This process is reversible. It looks like that the green light switches the protein to a state of conformation in which it has the fluorescence property, and at the same times excites the fluorescence; whereas the blue light switches the protein into a state of conformation without the fluorescence property. The protein is a protein naturally occurring in the sea anemone *anemonia sulcata*, the functions of which described here may be purposefully enhanced by exchanging amino acids.

Further, it is known from Nature Vol. 388 pages 355-358 (1997) that the green fluorescent protein (GFP) and mutants thereof may be switched between two states one of which differs from the other in a spectral aspect.

Both proteins mentioned here could be used as a fluorescence marker in living cells.

From Nature, Vol. 420 pages 759-760 (2002) fluorescent molecules from the family of diarylethenes are known which may be deliberately switched between a fluorescent and a non-fluorescent state. Both states are thermally stable so that the switching process can be accomplished at comparatively low intensities. In this case, the switching process is a photoisomerization. Such molecules can also be referred to as photochromic.

There is a particular need for a method of high spatial resolution imaging a structure of a sample which may be carried out with comparatively low cost and efforts with regard to the required apparatuses.

BRIEF SUMMARY OF THE INVENTION

A method of high spatial resolution measuring a sample, the sample in an area of interest containing a substance, the method comprising the steps of selecting the substance from a group of substances which are capable of being repeatedly transferred out of a first state having first optical properties into a second state having second optical properties by means of an optical switch over signal, and which are capable of returning out of the second state into the first state; of transferring the substance within areas of the sample into the second state by means of the optical switch over signal with which at least one spatially limited area of the sample is purposefully omitted, the at least one spatially limited area of the sample being directed on the area of interest of the sample; and of detecting an optical measurement signal, which is associated with the substance in the first state and which comes out of a detection area including both the area purposefully omitted with the switch over signal and areas in which the substance has been transferred into to second state.

In a second aspect, the invention provides a method of high spatial resolution imaging a structure of a sample, the structure being marked with a substance, the method comprising the steps of selecting the substance from a group of substances which are capable of being repeatedly transferred out of a first state having first optical properties into a second state having second optical properties by means of an optical switch over signal, and which are capable of returning out of the second state into the first state; of transferring the substance within areas of the sample into the second state by means of the optical switch over signal with which at least one spatially limited area of the sample is purposefully omitted; of detecting an optical measurement signal, which is associated with the substance in the first state and which comes out of a detection area including both the area purposefully omitted with the switch over signal and areas in which the substance has been transferred into to second state; and of scanning the sample with the area purposefully omitted with the switch over signal.

In a Third aspect, the invention provides a method of high spatial resolution imaging a structure of a sample, the structure being marked with a substance, the method comprising the steps of selecting the substance from a group of substances which are capable of being repeatedly transferred out of a first state having first optical properties into a second state having second optical properties by means of an optical switch over signal, and which are capable of returning out of the second state into the first state; of transferring the substance within areas of the sample into the second state by means of the optical switch over signal with which at least one spatially limited area of the sample is purposefully omitted; of detecting an optical measurement signal, which is associated with the substance in the second state and which comes out of a detection area including both the area purposefully omitted with the switch over signal and areas in which the substance has been transferred into to second state; and of scanning the sample with the area purposefully omitted with the switch over signal.

In all three aspects of the invention the two states of the substance differ with regard to at least one of the following criteria: state of conformation of a molecule; structure formula of a molecule; spatial arrangement of atoms within a molecule; spatial arrangement of bonds within a molecule; attachment of further atoms to a molecule; attachment of further molecules to a molecule; grouping of single atoms; grouping of molecules; grouping of molecules and single atoms; spatial orientation of a molecule; orientation of adjacent molecules; order formed by a multitude of molecules; order formed by a multitude of single atoms; order formed by a multitude of molecules and single atoms.

BRIEF DESCRIPTION OF THE DRAWINGS

In the following the invention is further explained and described by means of preferred embodiments, details of which are shown in the attached drawings.

DETAILED DESCRIPTION OF THE INVENTION

Figure 1:
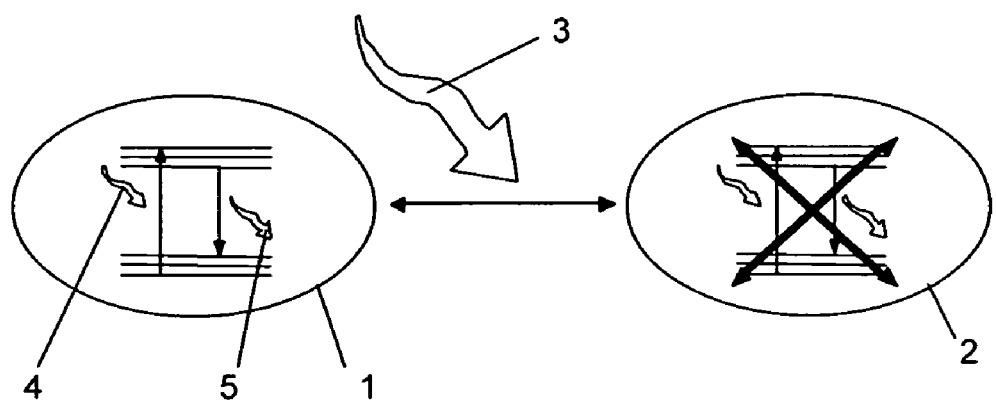
FIG. 1 symbolically shows two states of conformation of a molecule or a molecule complex, and FIG. 2 schematically shows a device for carrying out the invention.

Using substances having two states with different optical properties is a central aspect of the invention. Further, it is important that the substance may be purposefully switched with a switch over signal out of the first into the second state. This process is reversible. I.e. the substance can also be returned to the first state. The optical properties of the substance in the first state differ from those in the second state in that only the optical properties of the first state support the measurement signal. However, it is not necessary that the relevant optical properties are "binary", i.e. it is not necessary that they are present in the one state at 100% and in the other state at 0%. Instead, it is sufficient, if the relevant optical properties are different to such an extent that the measurement signal my at least mainly be regarded as associated with the first state.

In contrast to the state of the art in the field of fluorescence microscopy the invention makes no use of two simple energy states of a molecule, between which the molecule may be transferred by means of a simple energetic excitation. Instead, the two states differ at least with regard to one of the following criteria:
state of conformation of a molecule,
structure formula of a molecule,
spatial arrangement of atoms within a molecule,
spatial arrangement of bonds within a molecule,
attachment of further atoms or molecules to a molecule,
grouping of atoms and/or molecules,
spatial orientation of a molecule,
orientation of adjacent molecules,
order formed by a multitude of molecules and/or atoms.

The optical switch over signal for example accomplishes a re-arrangement of atom groups, a photo-isomerization, particularly a cis-trans-isomerization, a photo-cyclization, a protonation or de-protonation, a spinflip, an electron transfer and/or energy transfer between connected molecules or molecule subunits for transferring the corresponding substances out of their first into their second state.

With regard to the state of the art in the field of fluorescence microscopy, one advantage of the invention is that the states of the possible substances have a life time which is as a rule several times longer than the energy states typically involved in fluorescence. As a rule, the life time of the second state is at least 1 ns (nanosecond). A life time of at least 10 ns is preferred. Most preferred are thermally stable states. Further, the intensities which are necessary for achieving the change of state with the switch over signal are comparatively small. A large number of switching processes, in which the start state and/or the end state are quite long lived (>10 ns) may be effected and saturated with comparatively small intensities, as only comparatively slow and sometimes even no competing processes are existing.

The different optical properties of the two second states of the substance may be different spectral properties. For example, the first optical properties may differ from the second optical properties with regard to a different absorption of a probe signal, wherein the transmitted or reflected measurement signal may be observed. Different luminescences selected from the group including fluorescence, phosphorescence, electro-luminescence and chemo-luminescence are preferred as different spectral properties. Molecules changing their spectral properties, particularly their colour, which are suitable for marking the structure of interest in carrying out the present invention are also referred to as photochromic.

Instead of different spectral properties the two states of the substance may also have different polarization properties, for example with regard to an optical probe signal or with regard to a measurement signal emitted by the sample itself.

To the end of surpassing the diffraction limit with regard to the spatial resolution in the new method, the substance and the switch over signal are to be adapted to each other in such a way that the transfer out of the first state into the second state by means of the switch over signal is non-linearly correlated with the intensity of the switch over signal. This is achieved, when the transfer of the substance into the second stage completely or essentially completely takes place everywhere where the switch over signal exceeds a saturation threshold value. Particularly, the intensity of the switch over signal has to exceed the saturation threshold value everywhere in the detection area besides the purposefully omitted spatially limited area, and, at the same time, the purposefully omitted spatially limited area has to be a local intensity minimum of the switch over signal. Such a local intensity minimum having a zero intensity point may be provided by an interference pattern. In principle, projections may also be used to this end; further, it is possible to direct the switch over signal at a particular small or big angle from the side onto the sample. Additionally, holograms are possible for producing local minima of the switch over signal. However, smallest spatially limited areas which are omitted with the switch over signal may particularly easily be defined by the intensity minima of simple interference patterns.

Preferably, such substances are used in the new method, which may be transferred back out of the second to the first state by means of another switching signal. The other switching signal may be an optical signal like the switch over signal. It may, however, also be an electric or thermal signal, for example. Further, it is possible, that switching back to the first state occurs spontaneously, i.e. thermally driven already at room temperature. For example, it is known that molecules which undergo a photo-induced cis-trans-isomerisation can simply thermally return to their first state. By means of the other switching signal, however, the substance can purposefully be returned to the first state, which will be an advantage in accelerating the overall procedure.

The other switching signal is preferably applied prior to the switch over signal or after the detection of the measurement signal. If switching with the switch over signal is not affected by the other switching signal, the other switching signal may also be applied during application of the switch over signal to the sample. Further, it is not necessary to limit the other switching signal to the spatially limited area of interest, which reduces the efforts for applying optical switch signals and which is a precondition for using other kinds of switch signals at all.

If a probe signal is directed onto the sample for producing the measurement signal to be detected, the probe signal is applied to the sample after the switch over signal. Here, the probe signal may also be applied to the sample over a bigger area including the purposefully omitted spatially limited area. The spatial limitation required for increasing the spatial resolution of the new method is achieved by the switch over signal.

If the measurement signal is light emitted by the sample, a corresponding excitation signal should be applied after and/or during application of the switch over signal to the sample. In any case it should be applied to the sample later or at least not earlier than at the same time as the other switching signal, so far as the excitation signal and the other switching signal are not identical anyway.

For fully imaging a sample, it is required to scan the sample with the area purposefully omitted by the switch over signal, i.e. it is required to measure it in every point. To this end, the sample may at one point of time be simultaneously measured with regard to the measurement signal in a plurality of separated points, i.e. a plurality of spatially limited areas. Thus, a plurality of optical measurement signals, which are each associated with the substance in the first state and which are each coming out of one detection areas including one purposefully omitted area besides areas in which the substance is transferred into the second state, are detected separately but at the same time. Scanning may be accomplished by moving the switch signals, particularly the switch over signal, in three dimensions with regard to the coordinates of the sample. As all spatially limited areas omitted with the switch over signal are preferably intensity minima of an interference pattern, scanning can be accomplished by movement one intensity minimum or a plurality of interference minima of the switch over signal. This movement may be accomplished by a simple phase shift of the interfering beams.

Scanning the sample according to the new method results into a cyclic sequence of the steps: transferring the substance within areas of the sample into the second state by means of the optical switch over signal with which at least one spatially limited area of the sample is purposefully omitted; detecting an optical measurement signal, which is associated with the substance in the first state and which comes out of a detection area including both the area purposefully omitted with the switch over signal and areas in which the substance has been transferred into to second state; and transferring the substance into the first state. Here, it is sufficient, as already indicated above, that only the intensity minimum of the switch over signal is exactly directed onto the respective area of interest of the sample.

Preferably, the substance with the two different optical properties is selected from the group of proteins. This group particularly includes the known proteins asCP (asFP595) and their mutants T70A/A148S/S165V which have two conformational states with suitable optical properties, and also the green fluorescent protein (GFP) and mutants derived thereof.

Proteins as marker substances can be introduced into a biological sample by genetic engineering so that no subsequent marking of the structure (staining) of the sample is required which may affect the sample or which alters the sample at least by the step of marking or staining. If marking of the structure of interest of the sample in a genetic engineering way is not possible, the structure of the sample may be marked or stained with the substance in a usual way which is known as such. For example, agents may be used which selectively bond to the structure of interest and to which the substances is or will be bonded. A plurality of suitable procedures are known to those skilled in the art of staining samples for fluorescence microscopy. The sample may also intrinsically have molecules with suitable optical states which comply with the requirements for the substance for the new method.

After marking the structure with the fluorescent substance, the new imaging method can be carried out on a usual fluorescence microscope, the additional efforts for enhancing the resolution below the diffraction barrier being comparatively small and may be limited to means for providing the optical switch over signal. These means may, for example, comprise a simple laser or even a conventional lamp. In a preferred embodiment in which several areas are simultaneously measured for accelerating the method, the measurement signals from the individual areas are simultaneously read by a (CCD-)camera. The full image of the sample results from putting together a plurality of images with different positions of the measured areas in the sample.

The invention may also be carried out in that an optical measurement signal which is associated with the substance in the second state and which comes out of a detection area including both the area purposefully omitted with the switch over signal and areas in which the substance has been transferred into to second state is detected. In this embodiment of the new method, the information of interest about a particular point of a sample may be calculated from the variation of the optical measurement signal when scanning the sample with the area purposefully omitted with the switch over signal across the particular point. Also here, a sub-diffraction resolution in imaging the sample may be obtained because of the sub-diffraction spatial limitation of the area effectively omitted with the switch over signal.

FIG. 1 symbolically shows a molecule or a molecule complex which can be in two different states 1 and 2. The first state 1 of these two states is fluorescent; the second state 2 is not. By means of illuminating with a switch over signal 3 having a characteristic wave length 3 a purposeful change from the first state 1 to the second state 2 can be induced. In principle, the molecule may spontaneously return from the second state 2 to the first state 1. However, it is preferred, if both states 1 and 2 are thermally stable, and if a further optical switch signal is used for switching back into the first state 1.

Figure 2:
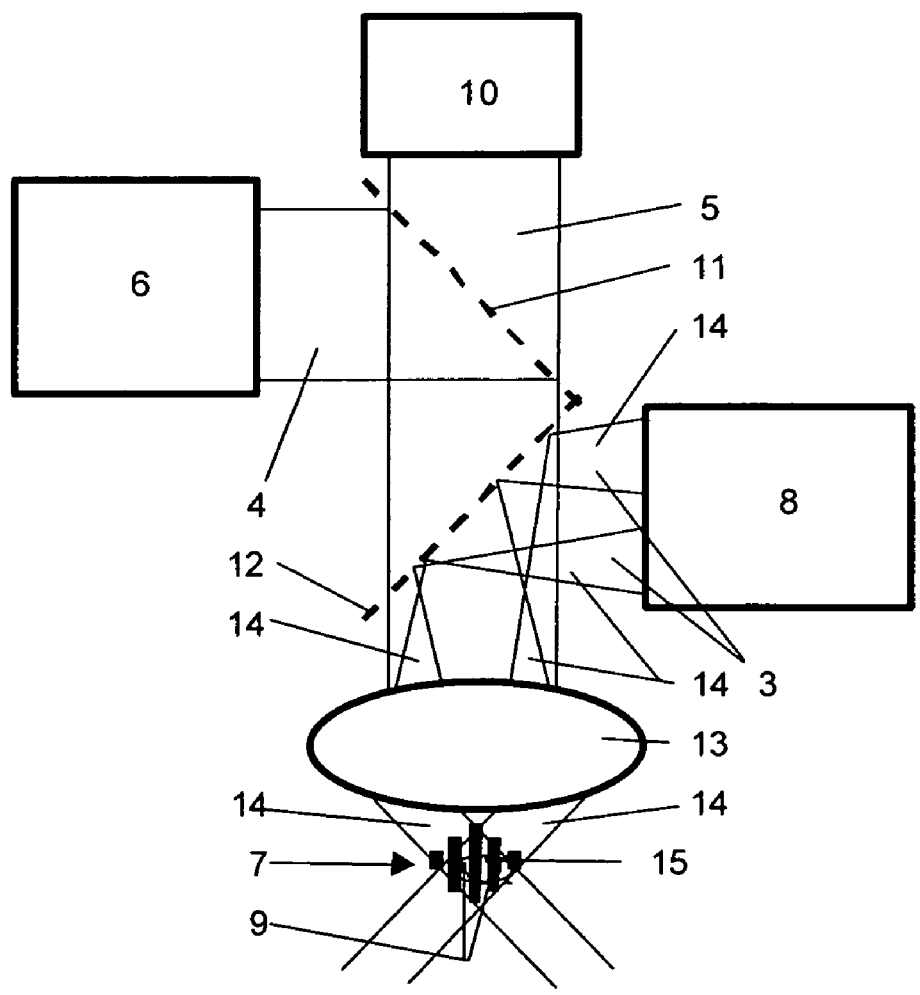

FIG. 2 schematically shows a suitable device for carrying out the invention. The device comprises two beam splitters 11 and 12 as well as an objective 13. A sample 7 is excited for fluorescence by an excitation signal which is used as a probe signal 4 and which comes from a fluorescent excitation unit, on the one hand; on the other hand, the sample is hindered from fluorescence at defined points by means of the switch over signal 3 coming from a fluorescence hindering unit 8 in that molecules at the defined points are reversibly brought into the second non-fluorescent state. In the example shown, this is accomplished by superimposed interfering beams 14. Thus, fluorescence can only be produced in small spatially limited areas 9 which, under suitable conditions like, for example, a saturation of the switch over process, are smaller than the diffraction limit. By means of a scanning movement of the interference pattern 15 and sequentially detecting and reading out the fluorescence as a measurement signal 5 by means of a camera 10, the whole sample 7 is imaged at a high resolution better than the diffraction limit.

Many variations and modifications may be made to the preferred embodiments of the invention without departing substantially from the spirit and principles of the invention. All such modifications and variations are intended to be included herein within the scope of the present invention, as defined by the following claims.

I claim:

1. A method of high spatial resolution measuring a sample, the sample in an area of interest containing a substance, the method comprising the steps of:

selecting the substance from a group of substances which are capable of being repeatedly transferred out of a first state having first optical properties into a second state having second optical properties by means of an optical switch over signal, and which are capable of returning out of the second state into the first state, the two states differing with regard to at least one of the following criteria:

state of conformation of a molecule, structure formula of a molecule, spatial arrangement of atoms within a molecule, spatial arrangement of bonds within a molecule, attachment of further atoms to a molecule, attachment of further molecules to a molecule, grouping of single atoms, grouping of molecules, grouping of molecules and single atoms, spatial orientation of a molecule, orientation of adjacent molecules, order formed by a multitude of molecules, order formed by a multitude of single atoms, order formed by a multitude of molecules and single atoms, transferring the substance within areas of the sample into the second state by means of the optical switch over signal with which at least one spatially limited area of the sample is purposefully omitted, the at least one spatially limited area of the sample being directed on the area of interest of the sample, and detecting an optical measurement signal, which is associated with the substance in the first state and which comes out of a detection area including both the area purposefully omitted with the switch over signal and areas in which the substance has been transferred into to second state.

2. The method of claim 1, wherein the life time of the second state is longer than 1 ns.

3. The method of claim 1, wherein the different optical properties of the first and the second states of the substance are different spectral properties.

4. The method of claim 3, wherein the first optical properties differ from the second optical properties with regard to a different absorption of a probe signal.

5. The method of claim 3, wherein the first optical properties differ from the second optical properties with regard to a different luminescence selected from the group including fluorescence, phosphorescence, electro-luminescence and chemo-luminescence.

6. The method of claim 1, wherein the different optical properties of the first and the second states of the substance are different polarization properties.

7. The method of claim 1, comprising the further step of adapting the substance and the switch over signal to each other in such a way that everywhere where the switch over signal exceeds a saturation threshold value the substance is essentially in its second state.

8. The method of claim 1, wherein the intensity of the switch over signal exceeds the saturation threshold value within the whole detection area besides the area purposefully omitted with the switch over signal, and wherein the area purposefully omitted with the switch over signal is a local intensity minimum of the switch over signal.

9. The method of claim 8, wherein the local intensity minimum of the switch over signal is an intensity minimum of an interference pattern, the intensity minimum having a zero intensity point.

10. The method of claim 1, wherein the substance is selected from the group of substances, wherein the substances within the group are capable of being transferred out of the second state into the first state by means of another switching signal.

11. The method of claim 10, wherein the other switching signal is applied to the sample essentially prior to the switch over signal.

12. The method of claim 10, wherein the other switching signal is applied to the sample essentially at the same time as the switch over signal.

13. The method of claim 10, wherein the other switching signal is applied to the sample across a bigger area including the detection area.

14. The method of claim 1, wherein a probe signal is applied to the sample essentially after the switch over signal.

15. The method of claim 14, wherein the probe signal is applied to the sample across a bigger area including the area purposefully omitted with the switch over signal.

16. The method of claim 5, wherein the substance is selected from the group of substances, wherein the substances within the group are capable of being transferred out of the second state into the first state by means of another switching signal which excites the luminescence and which is applied to the sample essentially during the application of the switch over signal.

17. A method of high spatial resolution imaging a structure of a sample, the structure being marked with a substance, the method comprising the steps of:
selecting the substance from a group of substances which are capable of being repeatedly transferred out of a first state having first optical properties into a second state having second optical properties by means of an optical switch over signal, and which are capable of returning out of the second state into the first state, the two states differing with regard to at least one of the following criteria:
state of conformation of a molecule,
structure formula of a molecule,
spatial arrangement of atoms within a molecule,
spatial arrangement of bonds within a molecule,
attachment of further atoms to a molecule,
attachment of further molecules to a molecule,
grouping of single atoms,
grouping of molecules,
grouping of molecules and single atoms,
spatial orientation of a molecule,
orientation of adjacent molecules,
order formed by a multitude of molecules,
order formed by a multitude of single atoms,
order formed by a multitude of molecules and single atoms,
transferring the substance within areas of the sample into the second state by means of the optical switch over signal with which at least one spatially limited area of the sample is purposefully omitted, and
detecting an optical measurement signal, which is associated with the substance in the first state and which comes out of a detection area including both the area purposefully omitted with the switch over signal and areas in which the substance has been transferred into to second state, the at least one spatially limited area of the sample being directed on the area of interest of the sample, and scanning the sample with the area purposefully omitted with the switch over signal.

18. The method of claim 17, wherein a plurality of optical measurement signals which are each associated with the substance in the first state and which are each coming out of one detection areas including one purposefully omitted area besides areas in which the substance is transferred into the second state are separately detected at the same time.

19. The method of claim 17, wherein the steps of
transferring the substance within areas of the sample into the second state by means of the optical switch over signal with which at least one spatially limited area of the sample is purposefully omitted, and
detecting an optical measurement signal, which is associated with the substance in the first state and which comes out of a detection area including both the area purposefully omitted with the switch over signal and areas in which the substance has been transferred into to second state, and the further step of transferring the substance into the first state, are successively executed for different spatially limited areas of the sample in a cyclic sequence.

20. The method of claim 17, wherein the substance with which the structure of the sample is marked is selected from a sub-group of substances which includes proteins.

21. The method of claim 17, wherein the substance with which the structure of the sample is marked is selected from a sub-group of substances which includes fluorescent proteins.

22. The method of claim 19, wherein a fluorescence microscope is used for successively executing the steps of
transferring the substance within areas of the sample into the second state by means of the optical switch over signal with which at least one spatially limited area of the sample is purposefully omitted,
detecting an optical measurement signal, which is associated with the substance in the first state and which comes out of a detection area including both the area purposefully omitted with the switch over signal and areas in which the substance has been transferred into to second state, and transferring the substance into the first state.

23. A method of high spatial resolution imaging a structure of a sample, the structure being marked with a substance, the method comprising the steps of:
selecting the substance from a group of substances which are capable of being repeatedly transferred out of a first state having first optical properties into a second state having second optical properties by means of an optical switch over signal, and which are capable of returning out of the second state into the first state, the two states differing with regard to at least one of the following criteria:
state of conformation of a molecule,
structure formula of a molecule,
spatial arrangement of atoms within a molecule,
spatial arrangement of bonds within a molecule,
attachment of further atoms to a molecule,
attachment of further molecules to a molecule,
grouping of single atoms,
grouping of molecules,
grouping of molecules and single atoms,
spatial orientation of a molecule,
orientation of adjacent molecules,
order formed by a multitude of molecules,
order formed by a multitude of single atoms, order formed by a multitude of molecules and single atoms, transferring the substance within areas of the sample into the second state by means of the optical switch over signal with which at least one spatially limited area of the sample is purposefully omitted, and detecting an optical measurement signal, which is associated with the substance in the second state and which comes out of a detection area including both the area purposefully omitted with the switch over signal and areas in which the substance has been transferred into to second state, the at least one spatially limited area of the sample being directed on the area of interest of the sample, and scanning the sample with the area purposefully omitted with the switch over signal.

24. A method of high spatial resolution imaging a structure of a sample, the structure being marked with a substance, the method comprising the steps of:

selecting the substance from a group of substances which are capable of being repeatedly transferred out of a first state having first optical properties into a second state having second optical properties by means of an optical switch over signal, and which are capable of returning out of the second state into the first state, the two states differing with regard to at least one of the following criteria:

state of conformation of a molecule, structure formula of a molecule, spatial arrangement of atoms within a molecule, spatial arrangement of bonds within a molecule, attachment of further atoms to a molecule, attachment of further molecules to a molecule, grouping of single atoms, grouping of molecules, grouping of molecules and single atoms, spatial orientation of a molecule, orientation of adjacent molecules, order formed by a multitude of molecules, order formed by a multitude of single atoms, order formed by a multitude of molecules and single atoms, transferring the substance within areas of the sample into the second state by means of the optical switch over signal with which at least one spatially limited area of the sample is purposefully omitted, and detecting an optical measurement signal, which is associated with the substance in the first state and which comes out of a detection area including both the area purposefully omitted with the switch over signal and areas in which the substance has been transferred into to second state, the at least one spatially limited area of the sample being directed on the area of interest of the sample, wherein a plurality of optical measurement signals which are each associated with the substance in the first state and which are each coming out of one detection areas including one purposefully omitted area besides areas in which the substance is transferred into the second state are separately detected at the same time, and scanning the sample with the area purposefully omitted with the switch over signal.

25. A method of high spatial resolution imaging a structure of a sample, the structure being marked with a substance, the method comprising the steps of:

selecting the substance from a group of substances which are capable of being repeatedly transferred out of a first state having first optical properties into a second state having second optical properties by means of an optical switch over signal, and which are capable of returning out of the second state into the first state, the two states differing with regard to at least one of the following criteria:

state of conformation of a molecule, structure formula of a molecule, spatial arrangement of atoms within a molecule, spatial arrangement of bonds within a molecule, attachment of further atoms to a molecule, attachment of further molecules to a molecule, grouping of single atoms, grouping of molecules, grouping of molecules and single atoms, spatial orientation of a molecule, orientation of adjacent molecules, order formed by a multitude of molecules, order formed by a multitude of single atoms, order formed by a multitude of molecules and single atoms, transferring the substance within areas of the sample into the second state by means of the optical switch over signal with which at least one spatially limited area of the sample is purposefully omitted, and detecting an optical measurement signal, which is associated with the substance in the second state and which comes out of a detection area including both the area purposefully omitted with the switch over signal and areas in which the substance has been transferred into to second state, the at least one spatially limited area of the sample being directed on the area of interest of the sample, wherein a plurality of optical measurement signals which are each associated with the substance in the second state and which are each coming out of one detection areas including one purposefully omitted area besides areas in which the substance is transferred into the second state are separately detected at the same time, and scanning the sample with the area purposefully omitted with the switch over signal.

* * * * *